United States Patent
Kim et al.

(10) Patent No.: US 10,551,512 B2
(45) Date of Patent: Feb. 4, 2020

(54) X-RAY DETECTOR AND X-RAY IMAGE SYSTEM USING THE SAME

(71) Applicant: LG ELECTRONICS INC., Seoul (KR)

(72) Inventors: Kangyoon Kim, Seoul (KR); Junghoon Lee, Seoul (KR); Jonggoo Park, Seoul (KR); Youngseok Yoon, Seoul (KR); Sungchul Hong, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 281 days.

(21) Appl. No.: 15/610,437

(22) Filed: May 31, 2017

(65) Prior Publication Data

US 2017/0350992 A1    Dec. 7, 2017

(30) Foreign Application Priority Data

Jun. 1, 2016 (KR) .......................... 10-2016-0067961

(51) Int. Cl.
 *G01T 1/20* (2006.01)
 *A61B 6/00* (2006.01)
 *G01N 23/04* (2018.01)

(52) U.S. Cl.
 CPC .......... *G01T 1/2018* (2013.01); *A61B 6/4208* (2013.01); *A61B 6/5205* (2013.01); *G01N 23/04* (2013.01)

(58) Field of Classification Search
 CPC ....... G01T 1/20; G01T 1/2018; G01T 1/2002; G01T 1/2012; G01T 1/2006; A61B 6/00; A61B 6/4208; A61B 6/5205; G01N 23/04
 USPC .................................. 378/62, 98, 98.2, 98.8
 See application file for complete search history.

(56) References Cited

U.S. PATENT DOCUMENTS

| | | | |
|---|---|---|---|
| 8,822,930 | B2 | 9/2014 | Soukal et al. |
| 2011/0210256 | A1 | 9/2011 | Mattson et al. |
| 2014/0284487 | A1 | 9/2014 | Sawada et al. |
| 2014/0301527 | A1 | 10/2014 | Morimoto et al. |
| 2016/0041272 | A1 | 2/2016 | Kondo et al. |

OTHER PUBLICATIONS

PCT International Application No. PCT/KR2017/005468, Notification of Transmittal of the International Search Report and the Written Opinion of the International Searching Authority, or Declaration dated Jul. 20, 2017, 11 pages.

*Primary Examiner* — Jurie Yun
(74) *Attorney, Agent, or Firm* — Lee, Hong, Degerman, Kang & Waimey

(57) ABSTRACT

An X-ray detector and an X-ray image system using the same are disclosed. The X-ray image system comprises an X-ray generator irradiating X-rays to an object to be photographed; an X-ray detector including a first photoelectric converter receiving X-rays transmitted the object and converting the X-rays in to a first electric signal and a second photoelectric converter converting the X-rays in to a second electric signal; a first image processor processing a first image of the object on the basis of the first electric signal of the X-ray detector; a second image processor processing a second image of the object on the basis of the second electric signal of the X-ray detector; a display module displaying the first and second processed images of the object; and a controller controlling the X-ray generator, the X-ray detector, the first and second image processors and the display module.

16 Claims, 21 Drawing Sheets

X-RAY DETECTOR AND X-RAY IMAGE SYSTEM USING THE SAME

CROSS REFERENCE TO RELATED APPLICATIONS

Pursuant to 35 U.S.C. § 119(a), this application claims the benefit of earlier filing date and right of priority to Korean Application No. 10-2016-0067961, filed on Jun. 1, 2016, the contents of which are all hereby incorporated by reference herein in its entirety.

BACKGROUND OF THE INVENTION

Field of the Invention

The present invention relates to an X-ray detector comprising a scintillator and an X-ray image system using the same.

Discussion of the Related Art

Generally, an X-ray detector is a system that transmits X-rays through an object, e.g., human body, and detects the amount of the transmitted X-rays to photograph the interior of the object.

The X-ray detector is generally used for a medical testing device and a non-destructive testing device.

In early days, an X-ray detector photographed the interior of an object by using an X-ray photosensitive film. However, such an X-ray detector has problems in that there is inconvenience to exchange the film with new one several times whenever the interior of an object is photographed and a memory for storing the film having the photographed interior of the object is additionally required.

Therefore, in recent years, an X-ray detector photographs the interior of an object by using a computed radiography (CR) method or a digital radiography (DR) method instead of the X-ray photosensitive film.

Such an X-ray detector may be implemented as a flat type X-ray detector based on a solid imaging element such as an active matrix, CCD, and CMOS.

The flat type X-ray detector may include a photoelectric conversion substrate converting light to an electric signal and a scintillator layer which is in contact with the photoelectric conversion substrate.

Therefore, if X-rays are irradiated to the scintillator layer, the flat type X-ray detector converts X-rays to light, and if the converted light enters the photoelectric conversion substrate, converts the light to an electric signal, thereby outputting X-ray photographed image or real-time X-ray image as a digital signal.

However, the existing X-ray detector may generate light loss due to diffusion and reflection of light as the light does not enter the photoelectric conversion substrate when X-rays are converted to the light in the scintillator layer.

Such light loss may deteriorate detection efficiency of X-rays, and may also deteriorate definition of X-ray photographed image.

Therefore, the development of an X-ray detector, which may improve definition of X-ray photographed image by increasing X-ray detection efficiency, will be required.

SUMMARY OF THE INVENTION

Accordingly, the present invention is directed to an X-ray detector and an X-ray image system using the same that substantially obviates one or more problems due to limitations and disadvantages of the related art.

An object of the present invention is to provide an X-ray detector and an X-ray image system using the same, in which photoelectric converters are respectively arranged on an upper surface and a lower surface of a scintillator layer to improve detection efficiency of X-rays.

Another object of the present invention is to provide an X-ray detector and an X-ray image system using the same, in which a thickness of a photoelectric converter disposed on an upper surface of a scintillator layer is reduced to enable a slim size and miniaturization.

Still another object of the present invention is to provide an X-ray detector and an X-ray image system using the same, in which a block layer is disposed between adjacent photoelectric conversion layers to improve picture quality of an image by using a small amount of X-rays.

Further still another object of the present invention is to provide an X-ray detector and an X-ray image system using the same, in which light paths are disposed in a scintillator layer to reduce light loss.

Further still another object of the present invention is to provide an X-ray detector and an X-ray image system using the same, in which total reflective films are disposed at both sides of a scintillator layer to reduce light loss.

Further still another object of the present invention is to provide an X-ray detector and an X-ray image system using the same, in which images acquired from a plurality of photoelectric converters are compared with each other to selectively display an image of high picture quality.

Further still another object of the present invention is to provide an X-ray detector and an X-ray image system using the same, in which images acquired from a plurality of photoelectric converters are overlapped with each other to improve picture quality of an image.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, an X-ray detector according to one embodiment of the present invention comprises a scintillator layer converting externally incident X-rays to light; and a photoelectric converter converting the converted light to an electric signal, wherein the photoelectric converter includes a first photoelectric converter disposed on an upper surface of the scintillator layer where the X-rays enter, and a second photoelectric converter disposed on a lower surface of the scintillator layer.

In another aspect of the present invention, an X-ray image system using an X-ray detector comprises an X-ray generator irradiating X-rays to an object to be photographed; an X-ray detector including a first photoelectric converter receiving X-rays transmitted the object and converting the X-rays to a first electric signal and a second photoelectric converter converting the X-rays to a second electric signal; a first image processor processing a first image of the object on the basis of the first electric signal of the X-ray detector; a second image processor processing a second image of the object on the basis of the second electric signal of the X-ray detector; a display module displaying the first and second processed images of the object; and a controller controlling the X-ray generator, the X-ray detector, the first and second image processors and the display module.

It is to be understood that both the foregoing general description and the following detailed description of the present invention are exemplary and explanatory and are intended to provide further explanation of the invention as claimed.

BRIEF DESCRIPTION OF THE DRAWINGS

Arrangements and embodiments may be described in detail with reference to the following drawings in which like reference numerals refer to like elements and wherein.

DETAILED DESCRIPTION OF THE INVENTION

Reference will now be made in detail to the preferred embodiments of the present specification, examples of which are illustrated in the accompanying drawings. Wherever possible, the same reference numbers will be used throughout the drawings to refer to the same or like parts. The suffixes "module" and "unit" for the elements used in the following description are given or used in common by considering facilitation in writing this disclosure only but fail to have meanings or roles discriminated from each other. Also, in description of the embodiments disclosed in this specification, if detailed description of the disclosure known in respect of the present invention is determined to make the subject matter of the embodiments disclosed in this specification obscure, the detailed description will be omitted. Also, the accompanying drawings are only intended to facilitate understanding of the embodiments disclosed in this specification, and it is to be understood that technical spirits disclosed in this specification are not limited by the accompanying drawings and the accompanying drawings include all modifications, equivalents or replacements included in technical spirits and technical scope of the present invention.

Although the terms such as "first" and/or "second" in this specification may be used to describe various elements, it is to be understood that the elements are not limited by such terms. The terms may be used to identify one element from another element.

The expression that an element is "connected" or "coupled" to another element should be understood that the element may directly be connected or coupled to another element, a third element may be interposed between the corresponding elements, or the corresponding elements may be connected or coupled to each other through a third element. On the other hand, the expression that an element is "directly connected" or "directly coupled" to another element" means that no third element exists therebetween.

It is to be understood that the singular expression used in this specification includes the plural expression unless defined differently on the context.

In this application, it is to be understood that the terms such as "include" and "has" are intended to designate that features, numbers, steps, operations, elements, parts, or their combination, which are disclosed in the specification, exist, and are intended not to previously exclude the presence or optional possibility of one or more other features, numbers, steps, operations, elements, parts, or their combinations.

Figure 1:
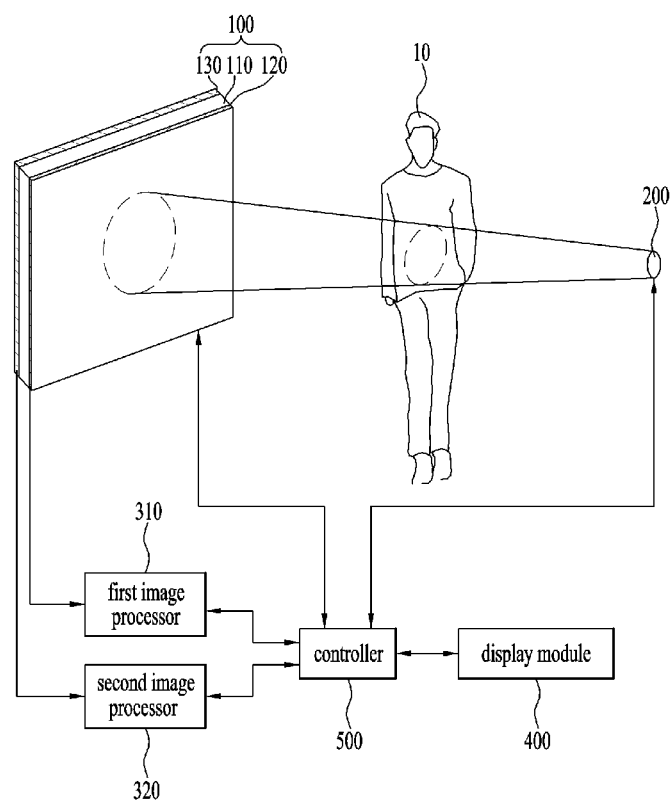
FIG. 1 is a block diagram illustrating an X-ray image system using an X-ray detector according to the present invention.

FIG. 1 is a block diagram illustrating an X-ray image system using an X-ray detector according to the present invention.

As shown in FIG. 1, an X-ray image system may include an X-ray generator 200, an X-ray detector 100, a first image processor 310, a second image processor 320, a display module 400, and a controller 500.

In this case, the X-ray generator 200 may irradiate X-rays to an object 10, which is desired to be photographed, in accordance with a control signal of the controller 500.

Then, the X-ray detector 100 may receive the X-rays transmitted the object 10 and convert the X-rays to electric signals. The X-ray detector 100 may include a first photoelectric converter 120 disposed on an upper surface of a scintillator layer 110, and a second photoelectric converter 130 disposed on a lower surface of the scintillator layer 110. For example, the scintillator layer 110 of the X-ray detector 100 converts the X-rays incident by transmitting the object 10 to light, the first photoelectric converter 120 converts the light converted by the scintillator layer 110 to a first electric signal, and the second photoelectric converter 130 converts the light converted by the scintillator layer 110 to a second electric signal.

The scintillator layer 110 may be made of CsI, NaI, LiF, GOS (Gadolinium Oxysulfide), or the like.

The first photoelectric converter 120 may include a first substrate having a plurality of pixel areas, a first photoelectric conversion layer disposed on the pixel areas of the first substrate, converting light to an electric signal, and a first transistor disposed between the first substrate and the first photoelectric conversion layer, outputting the converted electric signal.

Also, the second photoelectric converter 130 may include a second substrate having a plurality of pixel areas, a second photoelectric conversion layer disposed on the pixel areas of the second substrate, converting light to an electric signal, and a second transistor disposed between the second substrate and the second photoelectric conversion layer, outputting the converted electric signal.

Then, the first image processor 310 may electrically be connected to the first photoelectric converter 120 to process a first image of the object 10 on the basis of the first electric signal output from the first photoelectric converter 120.

The second image processor 320 may electrically be connected to the second photoelectric converter 130 to process a second image of the object 10 on the basis of the second electric signal output from the second photoelectric converter 130.

Subsequently, the display module 400 may display the first and second images of the object, which are processed from the first and second image processors 310 and 320.

Then, the controller 500 may control the X-ray generator 200, the X-ray detector 100, the first and second image processors 310 and 320, and the display module 400.

In this case, the controller 500 may synthesize the first image processed from the first image processor 310 with the second image processed from the second image processor 320 to display the synthesized image on the display module 400. This is because that an image of picture quality clearer than that of the first image acquired from the first photoelectric converter 120 disposed on the upper surface of the scintillator 110 or the second image acquired from the second photoelectric converter 130 disposed on the lower surface of the scintillator 110 if the first image and the second image are synthesized.

That is, the controller 500 may display a photographed image of an object in such a manner that the first image and the second image are synthesized, if the X-ray detector 100 has a structure that a first photoelectric conversion layer of the first photoelectric converter 120 disposed on the upper surface of the scintillator layer 110 and a second photoelectric conversion layer of the second photoelectric converter 130 disposed on the lower surface of the scintillator layer 110 are disposed to correspond to each other one to one. This is because that the first image acquired from the first photoelectric converter 120 and the second image acquired from the second photoelectric converter 130 are the same as each other if the first photoelectric conversion layer of the first photoelectric converter 120 disposed on the upper surface of the scintillator layer 110 and the second photoelectric conversion layer of the second photoelectric converter 130 disposed on the lower surface of the scintillator layer 110 are disposed to correspond to each other one to one.

Therefore, the controller 500 may overlap the first image and the second image with each other to improve picture quality of the overlapped image area, and may obtain a clear image even though a small amount of incident X-rays are provided.

As another case, the controller 500 may synthesize some of the first image processed from the first image processor 310 with some of the second image processed from the second image processor 320 to display the synthesized image on the display module 400. This is because that an image of picture quality clearer than that of the first image acquired from the first photoelectric converter 120 disposed on the upper surface of the scintillator 110 or the second image acquired from the second photoelectric converter 130 disposed on the lower surface of the scintillator 110 if some of the first image and some of the second image are synthesized.

That is, the controller 500 may display a photographed image of an object in such a manner that some of the first image and some of the second image are synthesized, if the X-ray detector 100 has a structure that the first photoelectric conversion layer of the first photoelectric converter 120 disposed on the upper surface of the scintillator layer 110 and the second photoelectric conversion layer of the second photoelectric converter 130 disposed on the lower surface of the scintillator layer 110 are disposed alternately with each other. This is because that some of the first image acquired from the first photoelectric converter 120 and some of the second image acquired from the second photoelectric converter 130 are the same as each other if the first photoelectric conversion layer of the first photoelectric converter 120 disposed on the upper surface of the scintillator layer 110 and the second photoelectric conversion layer of the second photoelectric converter 130 disposed on the lower surface of the scintillator layer 110 are disposed alternately with each other.

Therefore, the controller 500 may overlap some of the first image and some of the second image with each other to improve picture quality of the overlapped image area, and may obtain a clear image even though a small amount of incident X-rays are provided.

As still another case, the controller 500 may compare picture quality of the first image processed from the first image processor 310 with picture quality of the second image processed from the second image processor 320 to display the image having higher picture quality on the display module 400. This is because that an image of clear picture quality may be obtained even though picture quality is deteriorated due to a defect occurring in the first image acquired from the first photoelectric converter 120 disposed on the upper surface of the scintillator 110 or the second image acquired from the second photoelectric converter 130 disposed on the lower surface of the scintillator 110.

Therefore, the controller 500 may obtain an image of high picture quality without breaking image photographing even though a defect occurs in the X-ray detector 100.

As further still another case, the controller 500 may display the first image processed from the first image processor 310 or the second image processed from the second image processor 320 on the display module 400 if intensity of X-rays is greater than a reference value, display the first image processed from the first image processor 310 on the display module 400 if intensity of X-rays is the reference value, and synthesize the first image processed from the first image processor 310 with the second image processed from the second image processor 320 to display the synthesized image on the display module 400 if intensity of X-rays is smaller than the reference value. This is because that picture quality of the first image acquired from the first photoelectric converter 120 disposed on the upper surface of the scintillator 110 may be clearer than picture quality of the second image acquired from the second photoelectric converter 130 disposed on the lower surface of the scintillator 110 as the first photoelectric converter 120 is disposed on an upper surface of the scintillator 110, where X-rays enter.

Therefore, if intensity of X-rays is greater than the reference value, since picture quality of the first image acquired from the first photoelectric converter 120 disposed on the upper surface of the scintillator 110 or picture quality of the second image acquired from the second photoelectric converter 130 disposed on the lower surface of the scintillator 110 is clear, the controller 500 may select any one of the first and second images. And, if intensity of X-rays is the reference value, since picture quality of the first image acquired from the first photoelectric converter 120 disposed on the upper surface of the scintillator 110 is clearer than picture quality of the second image acquired from the second photoelectric converter 130 disposed on the lower surface of the scintillator 110, the controller 500 may select the first image. Subsequently, if intensity of X-rays is smaller than the reference value, since picture quality of the first image acquired from the first photoelectric converter 120 disposed on the upper surface of the scintillator 110 and picture quality of the second image acquired from the second photoelectric converter 130 disposed on the lower surface of the scintillator 110 are all deteriorated, the controller 500 may synthesize the first image and the second image with each other.

As described above, according to the present invention, since the X-ray detector provided with the photoelectric converters disposed on the upper surface and the lower surface of the scintillator layer is used, detection efficiency of the X-rays may be increased, whereby picture quality of the image may be improved.

Figure 2:
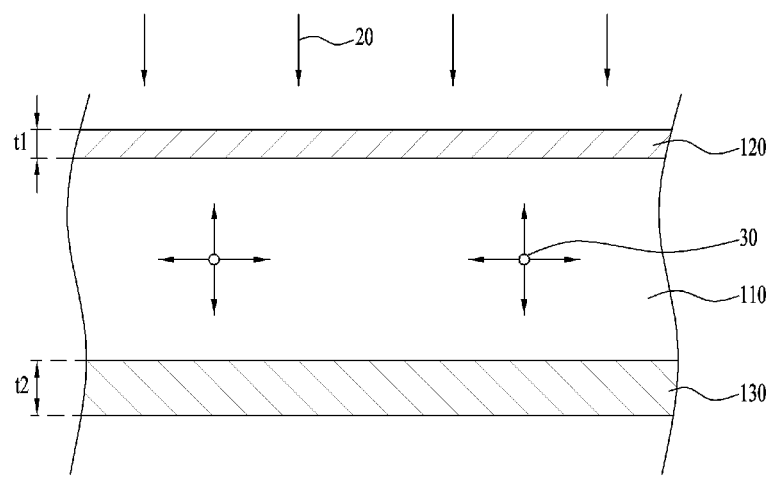
FIGS. 2 and 3 are structural cross-sectional diagrams illustrating an X-ray detector according to the first embodiment of the present invention.
Figure 3:
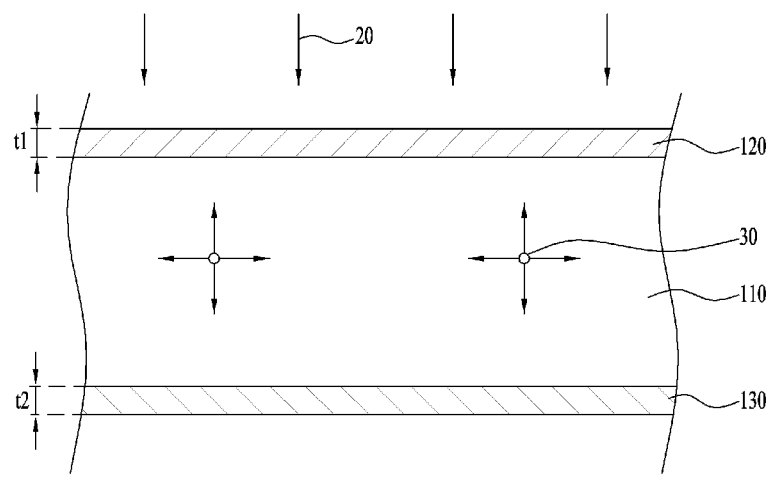

FIGS. 2 and 3 are structural cross-sectional diagrams illustrating an X-ray detector according to the first embodiment of the present invention.

As shown in FIGS. 2 and 3, the X-ray detector may include a scintillator layer 110 and a photoelectric conversion module that includes first and second photoelectric converters 120 and 130.

The scintillator layer 110 may convert externally incident X-rays 20 to light 30, and the photoelectric conversion module, which includes the first and second photoelectric converters 120 and 13, may convert the converted light to an electric signal.

In this case, the first photoelectric converter 120 may be disposed on an upper surface of the scintillator layer 110 where the X-rays 20 enter, and the second photoelectric converter 130 may be disposed on a lower surface of the scintillator layer 110.

For example, the scintillator layer 110 may be made of CsI, NaI, LiF, GOS (Gadolinium Oxysulfide), or the like.

The first photoelectric converter 120 may include a first substrate having a plurality of pixel areas, a first photoelectric conversion layer disposed on the pixel areas of the first substrate, converting light to an electric signal, and a first transistor disposed between the first substrate and the first photoelectric conversion layer, outputting the converted electric signal.

Also, the second photoelectric converter 130 may include a second substrate having a plurality of pixel areas, a second photoelectric conversion layer disposed on the pixel areas of the second substrate, converting light to an electric signal, and a second transistor disposed between the second substrate and the second photoelectric conversion layer, outputting the converted electric signal.

Subsequently, as shown in FIG. 2, a thickness t1 of the first photoelectric converter 120 may be different from a thickness t2 of the second photoelectric converter 130. For example, the thickness t1 of the first photoelectric converter 120 may be thinner than the thickness t2 of the second photoelectric converter 130. This is because that a too thick thickness of the first photoelectric converter 120 could lead to loss of some of the incident X-rays as the first photoelectric converter 120 is disposed on the upper surface of the scintillator layer 110 where the X-rays enter.

As the case may be, the thickness t1 of the first photoelectric converter 120 may be the same as the thickness t2 of the second photoelectric converter 130 as shown in FIG. 3.

As described above, according to the present invention, the thickness of the photoelectric converter disposed on the upper surface of the scintillator layer may be reduced to enable a slim size and miniaturization.

Figure 4:
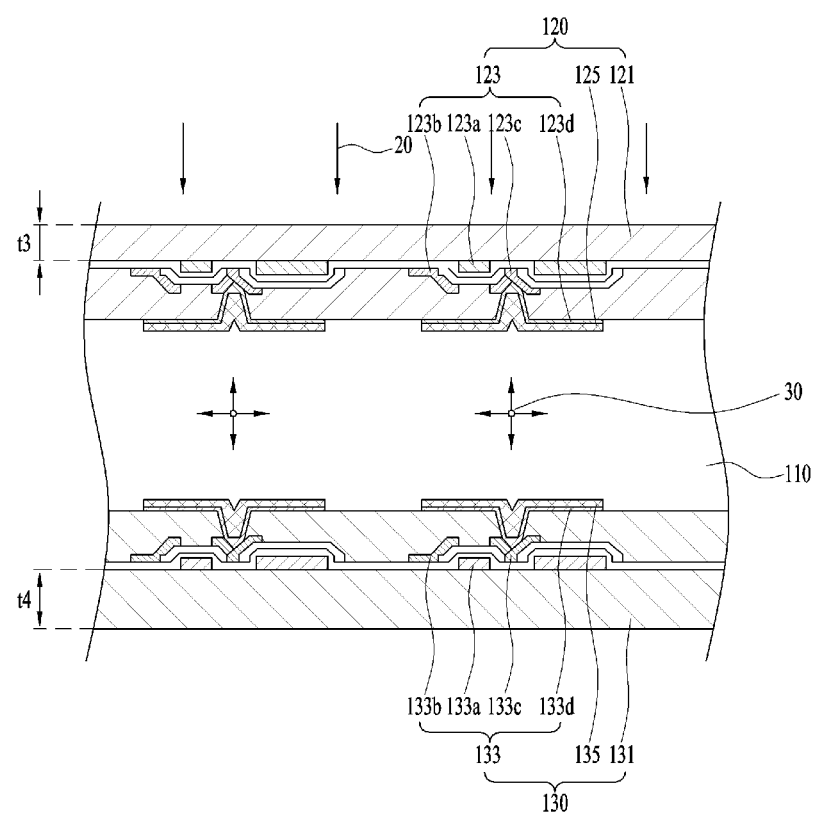
FIGS. 4 and 5 are structural cross-sectional diagrams illustrating an X-ray detector according to the second embodiment of the present invention.
Figure 5:
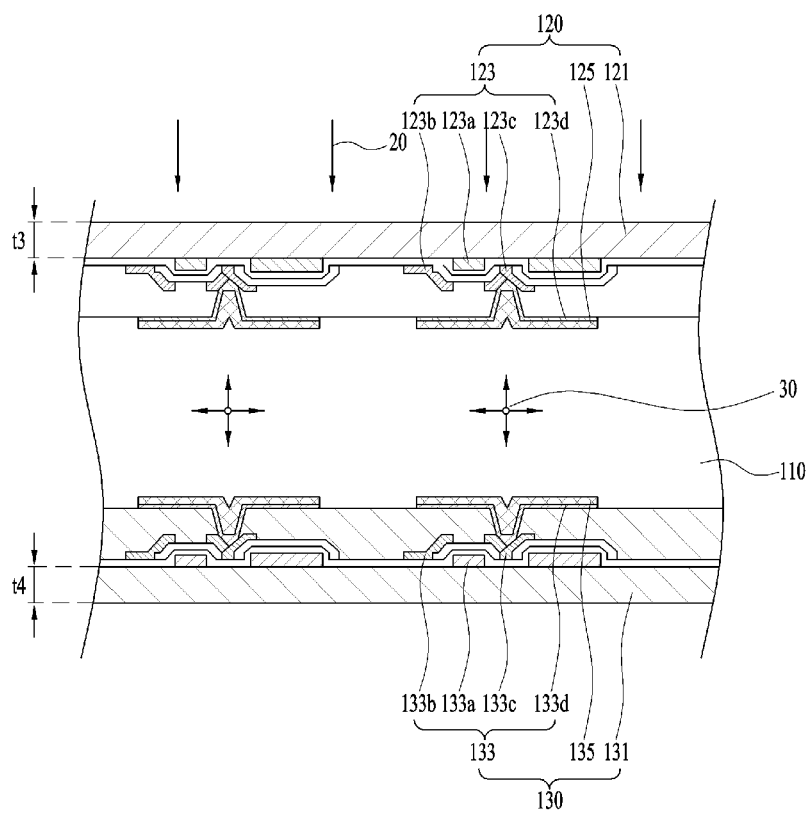

FIGS. 4 and 5 are structural cross-sectional diagrams illustrating an X-ray detector according to the second embodiment of the present invention.

As shown in FIGS. 4 and 5, the X-ray detector may include a scintillator layer 110 and a photoelectric conversion module that includes first and second photoelectric converters 120 and 130.

The first photoelectric converter 120 may include a first substrate 121 having a plurality of pixel areas, a first photoelectric conversion layer 125 disposed on the pixel areas of the first substrate 121, converting light to an electric signal, and a first transistor 123 disposed between the first substrate 121 and the first photoelectric conversion layer 125, outputting the converted electric signal. In this case, the first transistor 123 may include a gate electrode 123a, a source electrode 123b, a drain electrode 123c, and a pixel electrode 123d. The first photoelectric conversion layer 125 may be formed on the pixel electrode 123d of the first transistor 123.

Subsequently, the second photoelectric converter 130 may include a second substrate 131 having a plurality of pixel areas, a second photoelectric conversion layer 135 disposed on the pixel areas of the second substrate 131, converting light to an electric signal, and a second transistor 133 disposed between the second substrate 131 and the second photoelectric conversion layer 135, outputting the converted electric signal. In this case, the second transistor 133 may include a gate electrode 133a, a source electrode 133b, a drain electrode 133c, and a pixel electrode 133d. The second photoelectric conversion layer 135 may be formed on the pixel electrode 133d of the second transistor 133.

The first photoelectric conversion layer 125 of the first photoelectric converter 120 and the second photoelectric conversion layer 135 of the second photoelectric converter 130 may be disposed to correspond to each other one to one to face each other.

Meanwhile, as shown in FIG. 4, a thickness t3 of the first substrate 121 of the first photoelectric converter 120 may be different from a thickness t4 of the second substrate 131 of the second photoelectric converter 130. For example, the thickness t3 of the first substrate 121 of the first photoelectric converter 120 may be thinner than the thickness t4 of the second substrate 131 of the second photoelectric converter 130. This is because that a too thick thickness of the first substrate 121 of the first photoelectric converter 120 could lead to loss of some of the incident X-rays as the first photoelectric converter 120 is disposed on the upper surface of the scintillator layer 110 where the X-rays enter.

However, the thickness t3 of the first substrate 121 of the first photoelectric converter 120 may be the same as the thickness t4 of the second substrate 131 of the second photoelectric converter 130 as shown in FIG. 5.

As another case, X-ray transmittance of the first substrate 121 of the first photoelectric converter 120 may be different from X-ray transmittance of the second substrate 131 of the second photoelectric converter 130. For example, X-ray transmittance of the first substrate 121 of the first photoelectric converter 120 may be higher than X-ray transmittance of the second substrate 131 of the second photoelectric converter 130. This is because that low X-ray transmittance of the first substrate 121 of the first photoelectric converter 120 could lead to loss of some of the incident X-rays as the first photoelectric converter 120 is disposed on the upper surface of the scintillator layer 110 where the X-rays enter.

However, X-ray transmittance of the first substrate 121 of the first photoelectric converter 120 may be the same as X-ray transmittance of the second substrate 131 of the second photoelectric converter 130.

Also, each of the first substrate 121 of the first photoelectric converter 120 and the second substrate 131 of the second photoelectric converter 130 may be, but not limited to, at least any one of carbon, carbon fiber reinforced plastic, glass, crystal, sapphire, and metal, wherein the metal may be any one of Fe, Sn, Cr, and Al. In this case, the first substrate 121 of the first photoelectric converter 120 and the second substrate 131 of the second photoelectric converter 130 may be made of their respective materials different from each other depending on X-ray transmittance.

As described above, according to the present invention, the thickness of the substrate of the photoelectric converter disposed on the upper surface of the scintillator layer may be reduced, or X-ray transmittance of the substrate may be increased, whereby loss of incident X-rays may be minimized.

Figure 6:
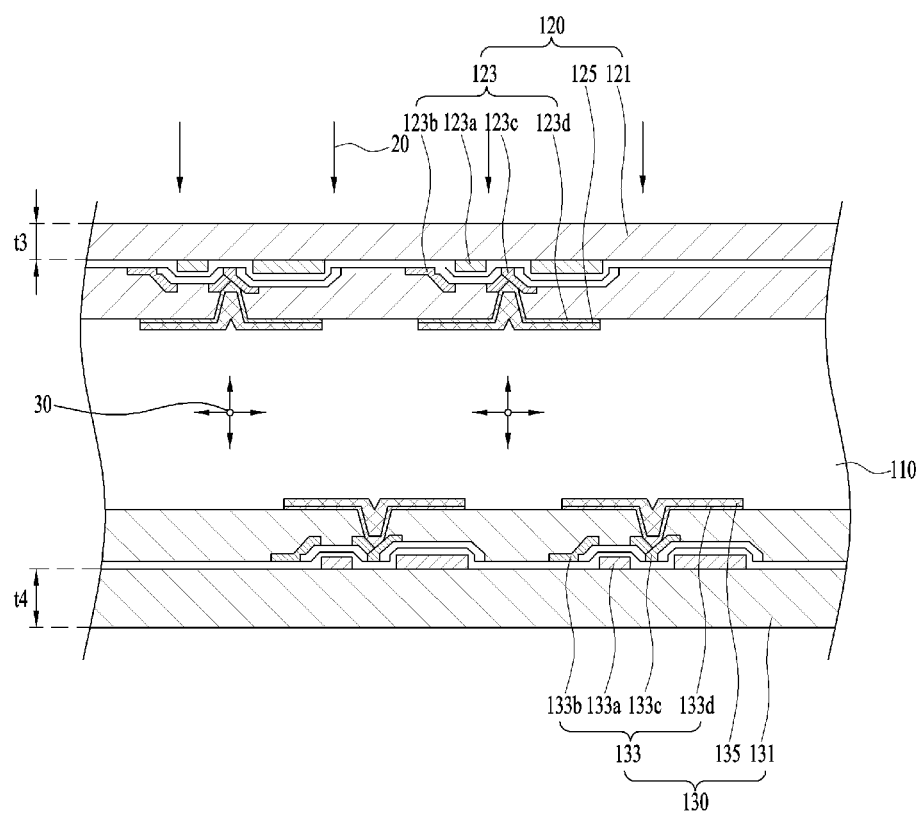
FIGS. 6 and 7 are structural cross-sectional diagrams illustrating an X-ray detector according to the third embodiment of the present invention.
Figure 7:
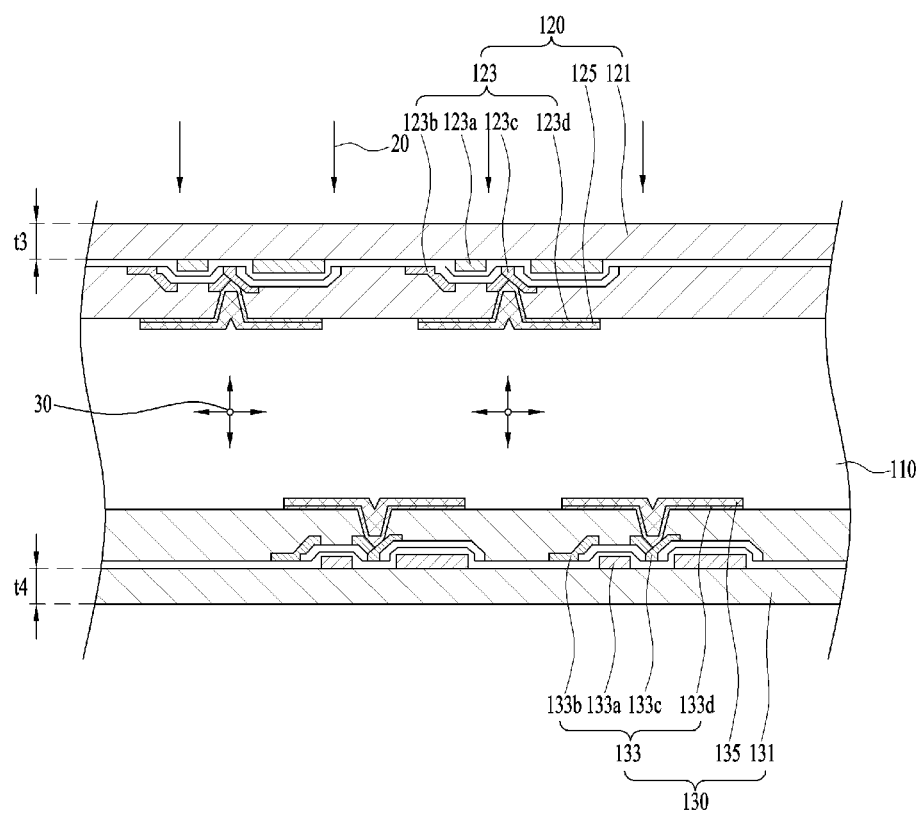

FIGS. 6 and 7 are structural cross-sectional diagrams illustrating an X-ray detector according to the third embodiment of the present invention.

As shown in FIGS. 6 and 7, the X-ray detector may include a scintillator layer 110 and a photoelectric conversion module that includes first and second photoelectric converters 120 and 130. The first photoelectric conversion layer 125 of the first photoelectric converter 120 and the second photoelectric conversion layer 135 of the second photoelectric converter 130 may be disposed alternately with each other. If the first photoelectric conversion layer 125 of the first photoelectric converter 120 and the second photoelectric conversion layer 135 of the second photoelectric converter 130 are disposed alternately with each other, since light may be detected uniformly without light loss from the entire area of the scintillator layer 110 as compared with the structure that the first photoelectric conversion layer 125 of the first photoelectric converter 120 and the second photoelectric conversion layer 135 of the second photoelectric converter 130 are disposed to correspond to each other, picture quality of the image may be improved.

Since the X-ray detector according to the third embodiment of the present invention is the same as the X-ray detector according to the second embodiment of the present invention except that the first photoelectric conversion layer 125 of the first photoelectric converter 120 and the second photoelectric conversion layer 135 of the second photoelectric converter 130 are disposed alternately with each other, its detailed description will be omitted.

Figure 8:
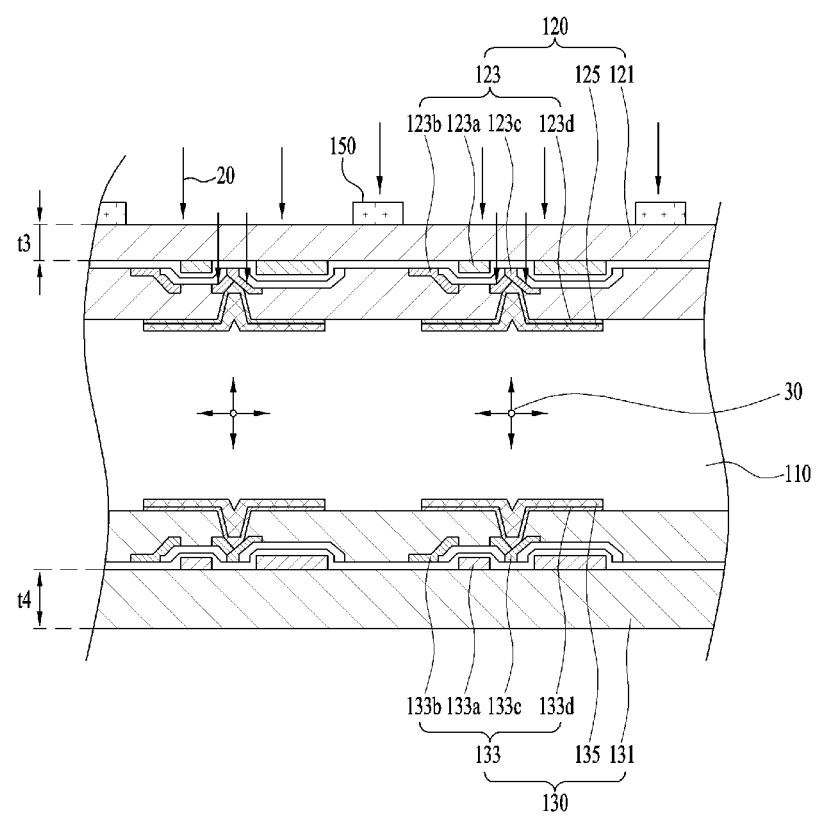
FIGS. 8 to 10 are structural cross-sectional diagrams illustrating an X-ray detector according to the fourth embodiment of the present invention.
Figure 9:
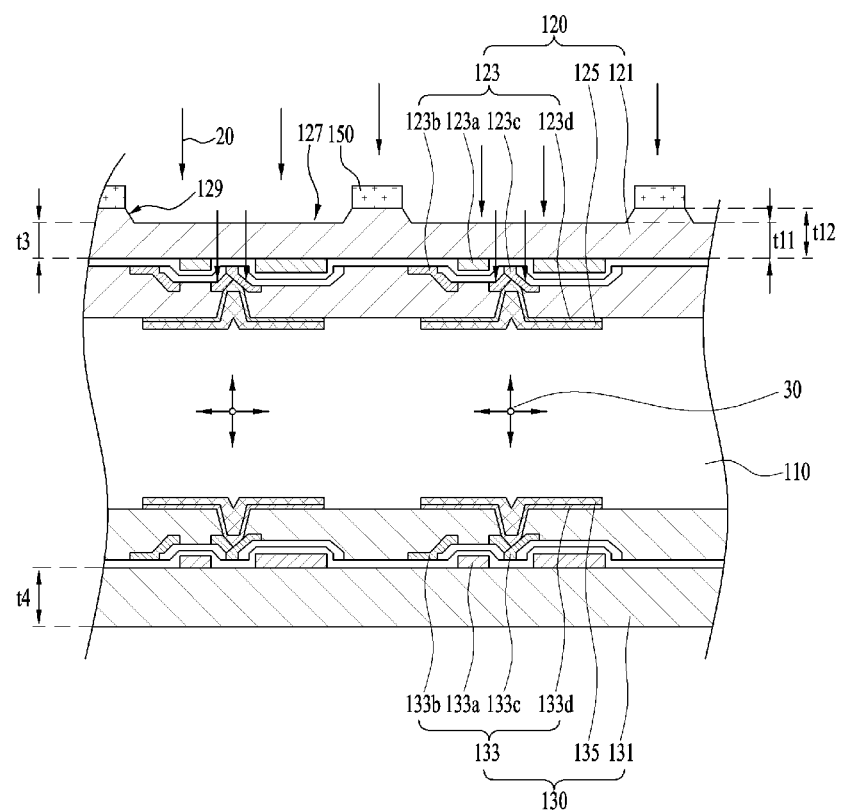
Figure 10:
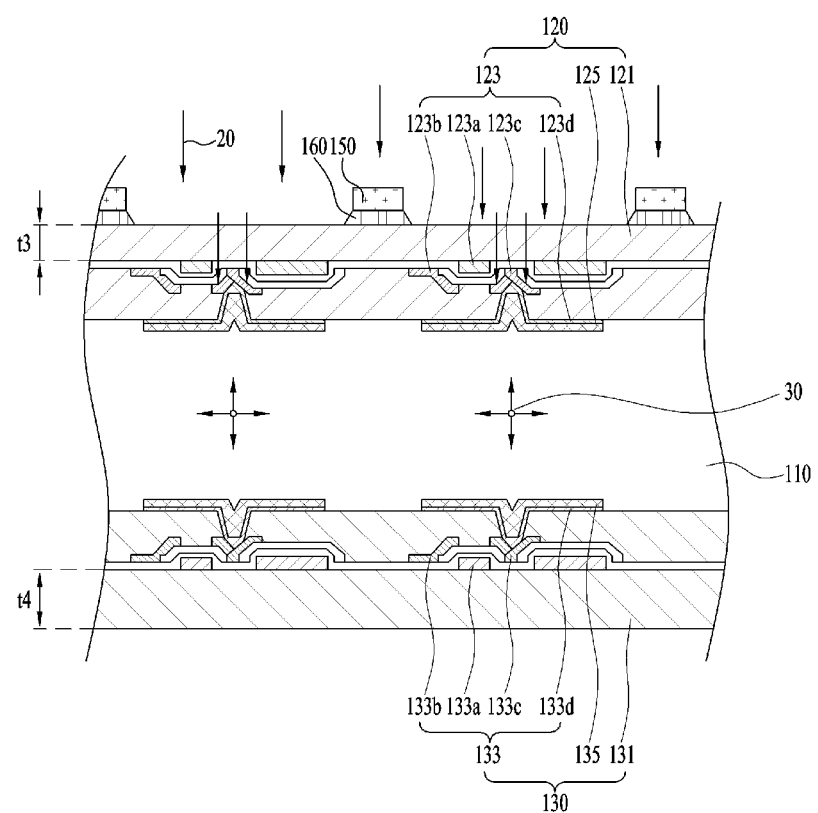

FIGS. 8 to 10 are structural cross-sectional diagrams illustrating an X-ray detector according to the fourth embodiment of the present invention.

As shown in FIGS. 8 to 10, the X-ray detector may include a scintillator layer 110 and a photoelectric conversion module that includes first and second photoelectric converters 120 and 130.

The first photoelectric converter 120 may include a first substrate 121 having a plurality of pixel areas, a first photoelectric conversion layer 125 disposed on the pixel areas of the first substrate 121, converting light to an electric signal, and a first transistor 123 disposed between the first substrate 121 and the first photoelectric conversion layer 125, outputting the converted electric signal. In this case, the first transistor 123 may include a gate electrode 123a, a source electrode 123b, a drain electrode 123c, and a pixel electrode 123d. The first photoelectric conversion layer 125 may be formed on the pixel electrode 123d of the first transistor 123.

Subsequently, the second photoelectric converter 130 may include a second substrate 131 having a plurality of pixel areas, a second photoelectric conversion layer 135 disposed on the pixel areas of the second substrate 131, converting light to an electric signal, and a second transistor 133 disposed between the second substrate 131 and the second photoelectric conversion layer 135, outputting the converted electric signal. In this case, the second transistor 133 may include a gate electrode 133a, a source electrode 133b, a drain electrode 133c, and a pixel electrode 133d. The second photoelectric conversion layer 135 may be formed on the pixel electrode 133d of the second transistor 133.

Meanwhile, the first substrate of the first photoelectric converter 120 may include a block layer 150 that blocks incident X-rays 20. In this case, the block layer 150 may be disposed between the first photoelectric conversion layers 125 which are adjacent to each other. That is, the first photoelectric conversion layer 125 may be formed on a lower surface of the first substrate 121, which faces the scintillator layer 110, and the block layer 150 may be formed on the upper surface of the first substrate 121 where X-rays 20 enter. If the block layer 150 is formed, since the X-rays intensively enter the area where the first photoelectric conversion layer 125 is disposed, detection efficiency of light converted from the X-rays may be increased.

As the case may be, a thickness t12 of the area of the first substrate 121 where the block layer 150 is formed may be thicker than a thickness t11 of the other area of the first substrate 121 as shown in FIG. 9. For example, the first substrate 121 may be provided with a groove 127 formed between the block layers 150 which are adjacent to each other. In this case, a side 129 of the groove 127 may be inclined. This is because that the side 129 of the groove 127 may stably support the block layer 150.

As another case, the first substrate 121 may be provided with a support protrusion 160 formed on the area where the block layer 150 is formed, to support the block layer 150. In this case, the side of the support protrusion 160 may be inclined. This is because that the side of the support protrusion 160 may stably support the block layer 150. For example, the support protrusion 160 may be formed of a material different from that of the first substrate 121.

In the X-ray detector of FIGS. 8 to 10, the first photoelectric conversion layer 125 of the first photoelectric converter 120 and the second photoelectric conversion layer 135 of the second photoelectric converter 130 may be disposed to correspond to each other one to one to face each other, or may be disposed alternately with each other as the case may be.

The thickness t3 of the first substrate 121 of the first photoelectric converter 120 may be thinner than the thickness t4 of the second substrate 131 of the second photoelectric converter 130. Since the first photoelectric converter 120 is disposed on the upper surface of the scintillator layer 110 where the X-rays enter, if the thickness t3 of the first substrate 121 of the first photoelectric converter 120 is too thick, it could lead to loss of some of the incident X-rays. Therefore, the thickness t3 of the first substrate 121 is thicker than the thickness t4 of the second substrate 131.

However, the thickness t3 of the first substrate 121 of the first photoelectric converter 120 may be the same as the thickness t4 of the second substrate 131 of the second photoelectric converter 130.

As another case, X-ray transmittance of the first substrate 121 of the first photoelectric converter 120 may be higher than X-ray transmittance of the second substrate 131 of the second photoelectric converter 130. This is because that low X-ray transmittance of the first substrate 121 of the first photoelectric converter 120 could lead to loss of some of the incident X-rays as the first photoelectric converter 120 is disposed on the upper surface of the scintillator layer 110 where the X-rays enter.

However, X-ray transmittance of the first substrate 121 of the first photoelectric converter 120 may be the same as X-ray transmittance of the second substrate 131 of the second photoelectric converter 130.

As described above, according to the present invention, the block layer may be disposed between the photoelectric conversion layers adjacent to each other to improve picture quality of an image through a small amount of X-rays, whereby an exposure rate may be minimized.

Figure 11:
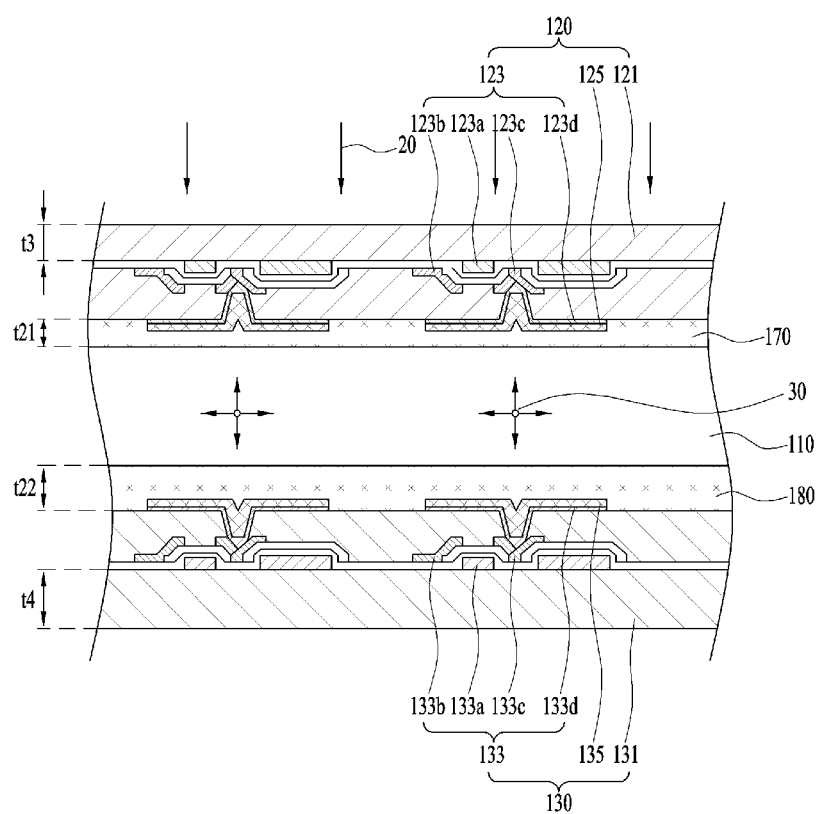
FIGS. 11 and 12 are structural cross-sectional diagrams illustrating an X-ray detector according to the fifth embodiment of the present invention.
Figure 12:
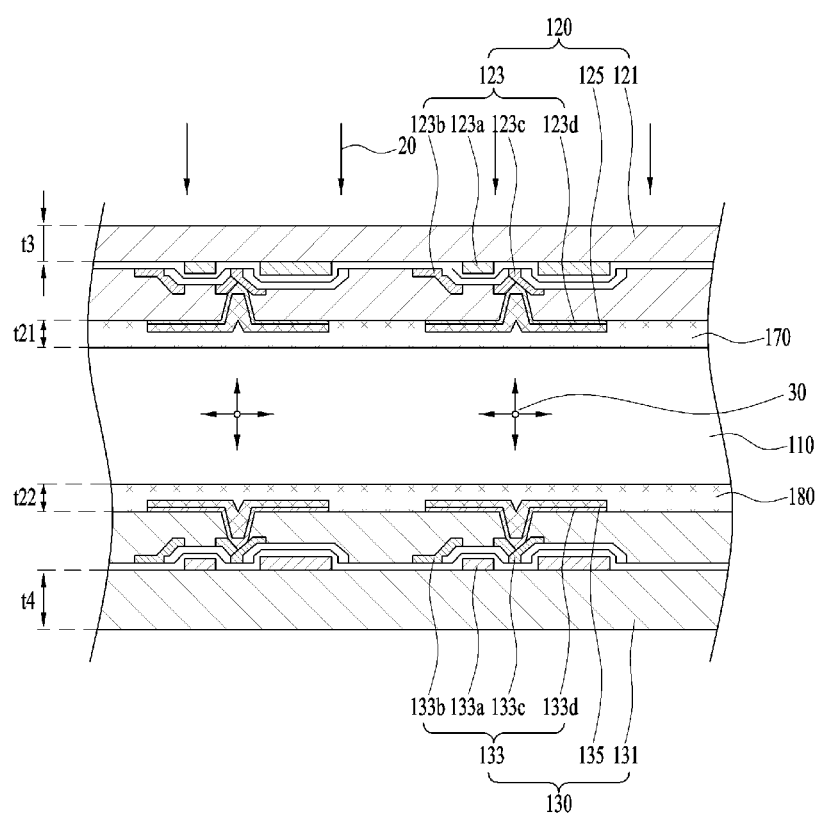

FIGS. 11 and 12 are structural cross-sectional diagrams illustrating an X-ray detector according to the fifth embodiment of the present invention.

As shown in FIGS. 11 and 12, the X-ray detector may include a scintillator layer 110 and a photoelectric conversion module that includes first and second photoelectric converters 120 and 130.

The first photoelectric converter 120 may include a first photoelectric conversion layer 125 disposed on pixel areas of a first substrate 121, converting light to an electric signal, and the second photoelectric converter 130 may include a second photoelectric conversion layer 135 disposed on pixel areas of a second substrate 131, converting light to an electric signal. In this case, although the first and second photoelectric conversion layers 125 and 135 may directly be in contact with the scintillator layer 110, the first and second photoelectric conversion layers 125 and 135 may be disposed to be spaced apart from the scintillator layer 110 at a certain interval as shown in FIGS. 11 and 12.

As shown in FIGS. 11 and 12, if the first and second photoelectric conversion layers 125 and 135 are disposed to be spaced apart from the scintillator layer 110 at a certain interval, a first adhesive layer 170 may be formed between the first photoelectric conversion layer 125 and the scintillator layer 110, and a second adhesive layer 180 may be formed between the second photoelectric conversion layer 135 and the scintillator layer 110. This is to prevent the scintillator layer 180 and the photoelectric conversion layers from being detached from each other by external impact. In this case, as shown in FIG. 11, a thickness t21 of the first adhesive layer 170 may be thinner than a thickness t22 of the second adhesive layer 180. This is because that a too thick thickness of the first adhesive layer 170 could lead to loss of some of incident X-rays as the first adhesive layer 170 is disposed on the upper surface of the scintillator layer 110 where the X-rays enter.

However, as shown in FIG. 12, the thickness t21 of the first adhesive layer 170 may be the same as the thickness t22 of the second adhesive layer 180.

Also, in the X-ray detector of FIGS. 11 and 12, the first photoelectric conversion layer 125 of the first photoelectric converter 120 and the second photoelectric conversion layer 135 of the second photoelectric converter 130 may be disposed to correspond to each other one to one to face each other, or may be disposed alternately with each other as the case may be.

The thickness t3 of the first substrate 121 of the first photoelectric converter 120 may be thinner than the thickness t4 of the second substrate 131 of the second photoelectric converter 130. This is because that a too thick thickness of the first substrate 121 of the first photoelectric converter 120 could lead to loss of some of the incident X-rays as the first photoelectric converter 120 is disposed on the upper surface of the scintillator layer 110 where the X-rays enter.

However, the thickness t3 of the first substrate 121 of the first photoelectric converter 120 may be the same as the thickness t4 of the second substrate 131 of the second photoelectric converter 130.

As another case, X-ray transmittance of the first substrate 121 of the first photoelectric converter 120 may be higher than X-ray transmittance of the second substrate 131 of the second photoelectric converter 130. This is because that low X-ray transmittance of the first substrate 121 of the first photoelectric converter 120 could lead to loss of some of the incident X-rays as the first photoelectric converter 120 is disposed on the upper surface of the scintillator layer 110 where the X-rays enter.

However, X-ray transmittance of the first substrate 121 of the first photoelectric converter 120 may be the same as X-ray transmittance of the second substrate 131 of the second photoelectric converter 130.

As described above, according to the present invention, the thickness of the adhesive layer disposed on the upper surface of the scintillator layer may be reduced, whereby loss of the incident X-rays may be minimized.

Figure 13:
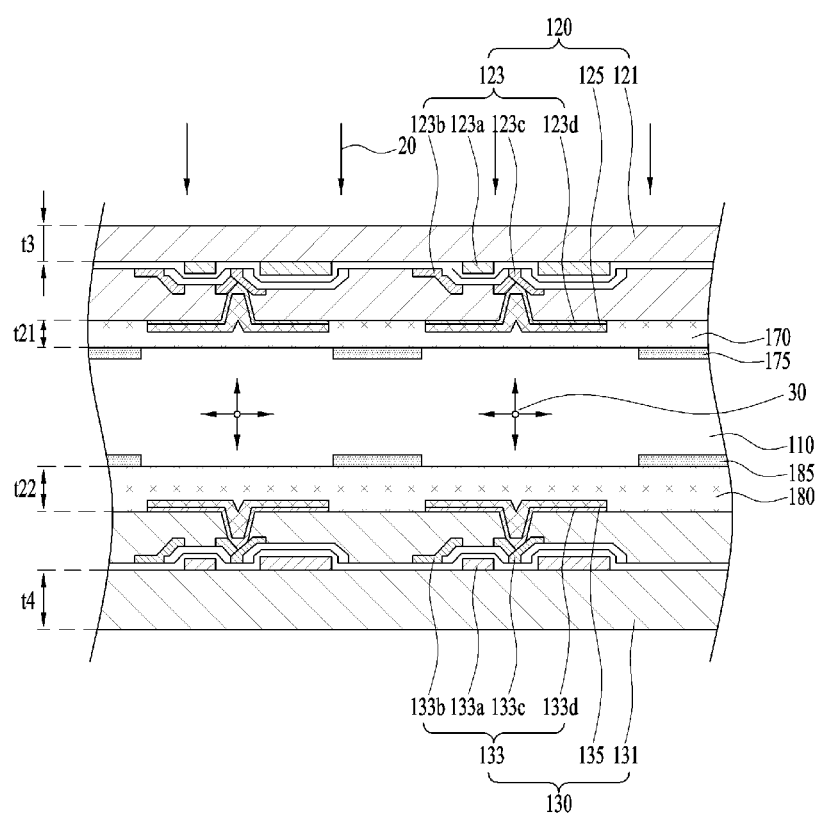
FIG. 13 is a structural cross-sectional diagram illustrating an X-ray detector according to the sixth embodiment of the present invention.

FIG. 13 is a structural cross-sectional diagram illustrating an X-ray detector according to the sixth embodiment of the present invention.

As shown in FIG. 13, in the X-ray detector, the first and second photoelectric conversion layers 125 and 135 are disposed to be spaced apart from the scintillator layer 110 at a certain interval, wherein the first adhesive layer 170 may be formed between the first photoelectric conversion layer 125 and the scintillator layer 110, and the second adhesive layer 180 may be formed between the second photoelectric conversion layer 135 and the scintillator layer 180. In this case, the first adhesive layer 170 may be provided with a first reflective layer 175 formed between the first photoelectric conversion layers 125 adjacent to each other, and the second adhesive layer 180 may be provided with a second reflective layer 185 formed between the second photoelectric conversion layers 135 adjacent to each other. The first and second reflective layers 175 and 185 are formed to block loss of light 30 converted within the scintillator layer 110 from an area between the first photoelectric conversion layers 125 and an area between the second photoelectric conversion layers 135. For example, the first and second reflective layers 175 and 185 may be made of metal having high reflectivity such as Al, Ni, Cu, Pd and Ag. As the case may be, the first and second reflective layers 175 and 185 may be made of their respective materials different from each other.

Since the X-ray detector according to the sixth embodiment of the present invention is the same as the X-ray detector according to the fifth embodiment of the present invention except that the first reflective layer 175 and the second reflective layer 185 are disposed, its detailed description will be omitted.

Figure 14:
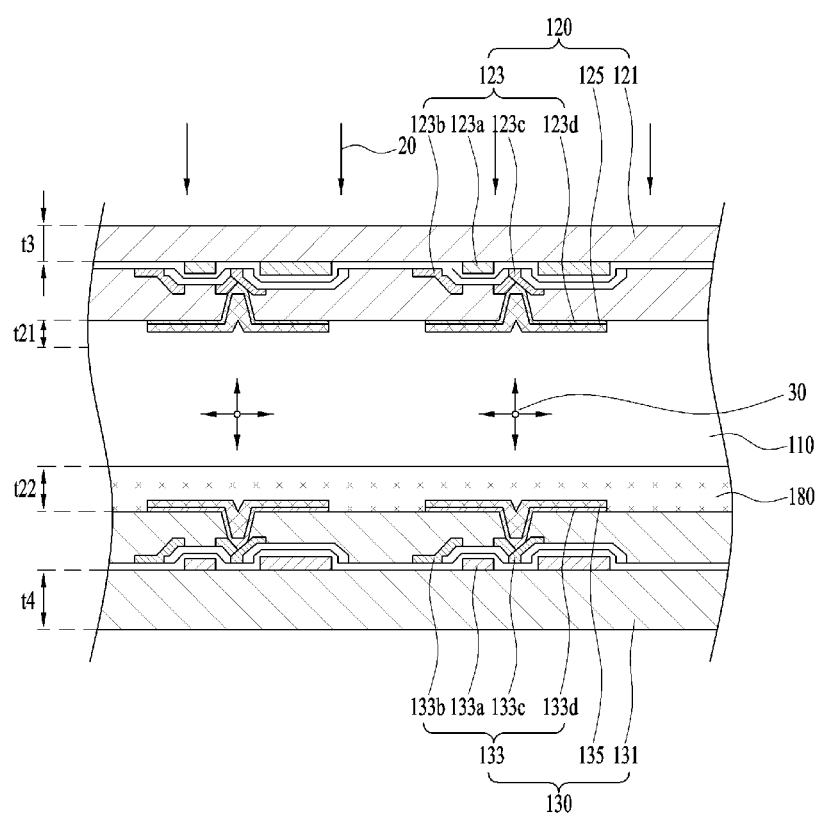
FIG. 14 is a structural cross-sectional diagram illustrating an X-ray detector according to the seventh embodiment of the present invention.

FIG. 14 is a structural cross-sectional diagram illustrating an X-ray detector according to the seventh embodiment of the present invention.

As shown in FIG. 14, in the X-ray detector, the first photoelectric conversion layer 125 may directly be in contact with the scintillator layer 110, and the second photoelectric conversion layer 135 may be disposed to be spaced apart from the scintillator layer 110 at a certain interval. In this case, the second adhesive layer 180 may be formed between the second photoelectric conversion layer 135 and the scintillator layer 110. The second adhesive layer 180 is formed to prevent the scintillator layer 180 and the second photoelectric conversion layer 135 from being detached from each other by external impact. As shown in FIG. 14, the first adhesive layer 180 is not formed between the first photoelectric conversion layer 125 and the scintillator layer 110 but the second adhesive layer 180 is formed between the second photoelectric conversion layer 135 and the scintillator layer 110. This is because that the adhesive layer formed between the first photoelectric conversion layer 125 and the scintillator layer 110 could lead to loss of some of the X-rays as the first photoelectric conversion layer 125 is disposed on the upper surface of the scintillator layer 110 where the X-rays enter.

Since the X-ray detector according to the seventh embodiment of the present invention is the same as the X-ray detector according to the fifth embodiment of the present invention except that the second adhesive layer 180 is only formed between the second photoelectric conversion layer 135 and the scintillator layer 110, its detailed description will be omitted.

Figure 15:
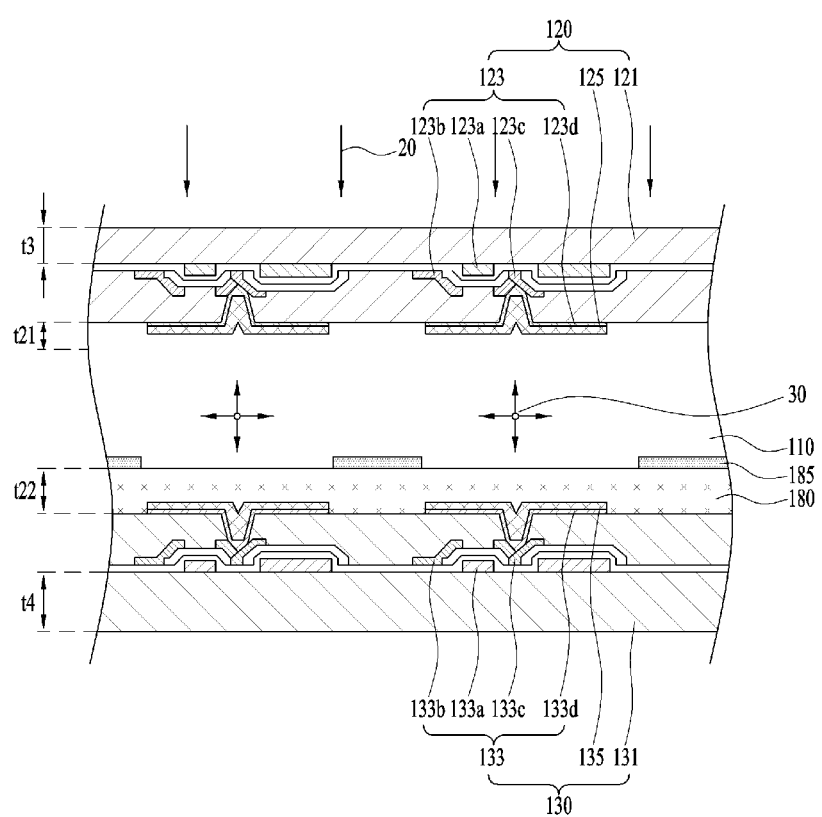
FIG. 15 is a structural cross-sectional diagram illustrating an X-ray detector according to the eighth embodiment of the present invention.

FIG. 15 is a structural cross-sectional diagram illustrating an X-ray detector according to the eighth embodiment of the present invention.

As shown in FIG. 15, in the X-ray detector, the first photoelectric conversion layer 125 may directly be in contact with the scintillator layer 110, and the second photoelectric conversion layer 135 may be disposed to be spaced apart from the scintillator layer 110 at a certain interval. In this case, the second adhesive layer 180 may be formed between the second photoelectric conversion layer 135 and the scintillator layer 110. The second adhesive layer 180 may be provided with the second reflective layer 185 formed between the second photoelectric conversion layers 135 adjacent to each other. In this case, the second reflective layer 185 is formed to block loss of light 30 converted within the scintillator layer 110 from an area between the second photoelectric conversion layers 135. For example, the second reflective layer 185 may be made of metal having high reflectivity such as Al, Ni, Cu, Pd and Ag.

Since the X-ray detector according to the eighth embodiment of the present invention is the same as the X-ray detector according to the seventh embodiment of the present invention except that the second adhesive layer 180 is only formed between the second photoelectric conversion layer 135 and the scintillator layer 110, its detailed description will be omitted.

Figure 16:
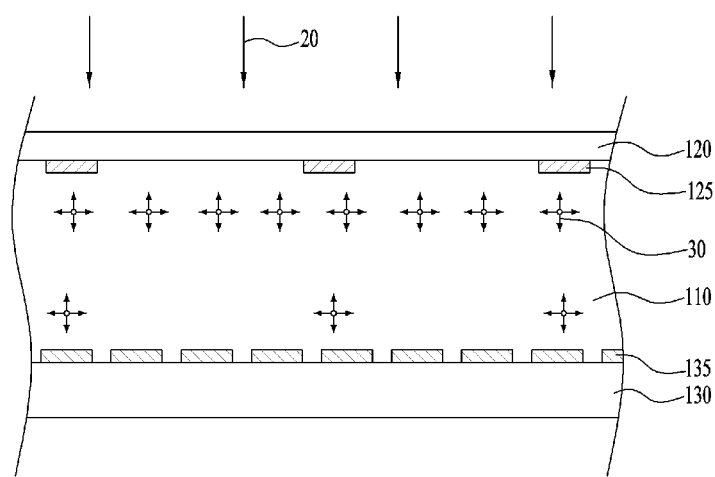
FIG. 16 is a structural cross-sectional diagram illustrating an X-ray detector according to the ninth embodiment of the present invention.

FIG. 16 is a structural cross-sectional diagram illustrating an X-ray detector according to the ninth embodiment of the present invention.

As shown in FIG. 16, the X-ray detector may include a scintillator layer 110 and a photoelectric conversion module that includes first and second photoelectric converters 120 and 130.

The first photoelectric converter 120 may include a first photoelectric conversion layer 125 disposed on pixel areas of a first substrate 121, converting light to an electric signal, and the second photoelectric converter 130 may include a second photoelectric conversion layer 135 disposed on pixel areas of a second substrate 131, converting light to an electric signal. In this case, the number of the first photoelectric conversion layers 125 may be different from the number of the second photoelectric conversion layers 135. For example, the number of the first photoelectric conversion layers 125 may be more than the number of the second photoelectric conversion layers 135. This is because that it may be difficult for the second photoelectric conversion layer 135 disposed on the lower surface of the scintillator layer 110 to detect light 30 as the amount of light converted in a lower area of the scintillator layer 110 is less than the amount of light converted in an upper area of the scintillator layer 110 where X-rays enter.

As described above, the number of the second photoelectric conversion layers 135 disposed on the lower surface of the scintillator layer 110 may be more than the number of the first photoelectric conversion layers 125 disposed on the upper surface of the scintillator layer 110, whereby light detection efficiency may be increased.

Figure 17:
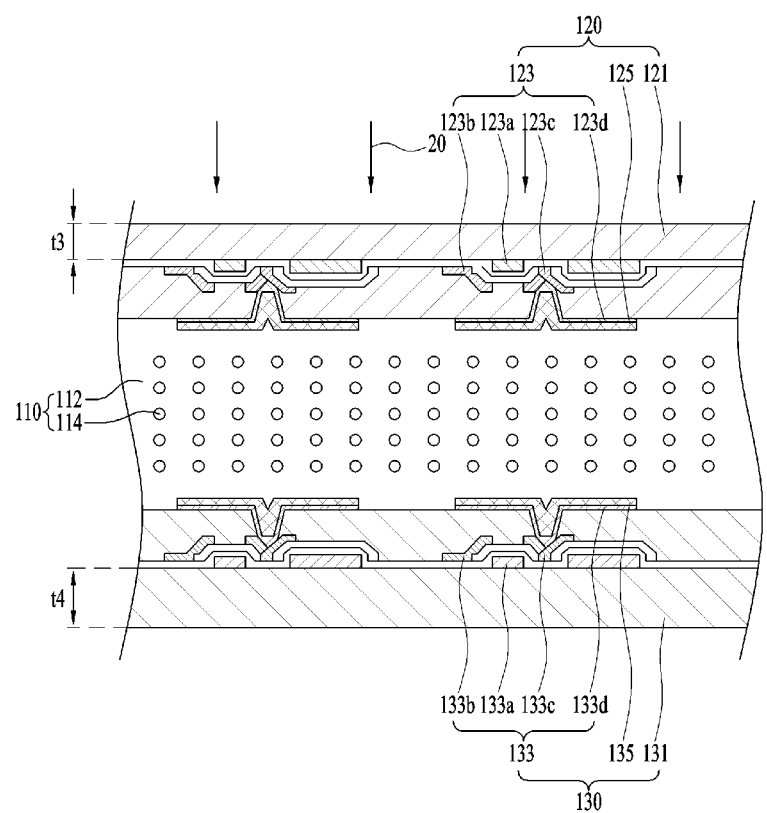
FIGS. 17 to 19 are structural cross-sectional diagrams illustrating an X-ray detector according to the tenth embodiment of the present invention.
Figure 18:
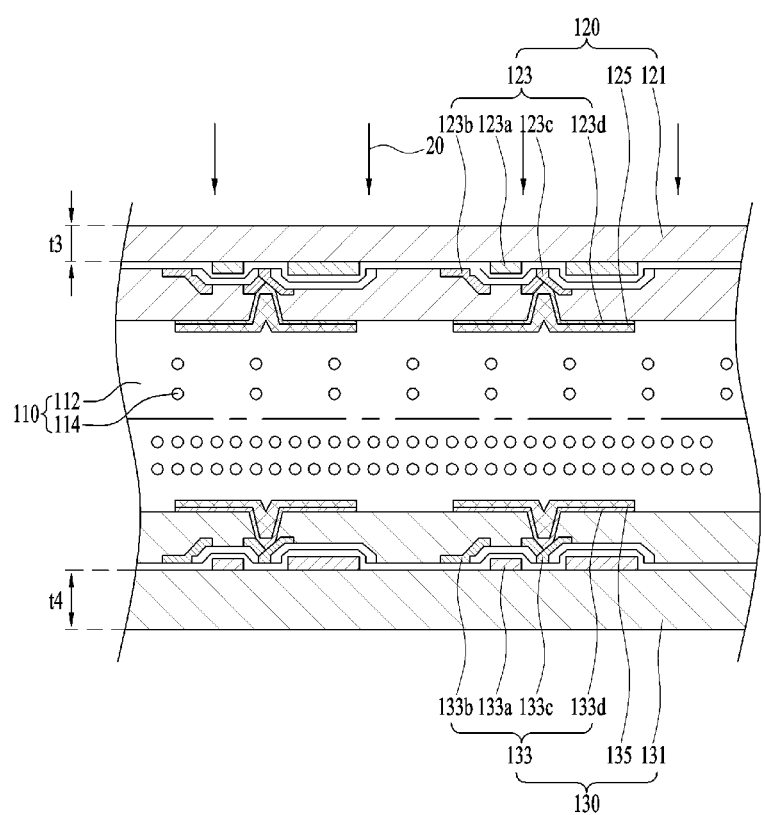
Figure 19:
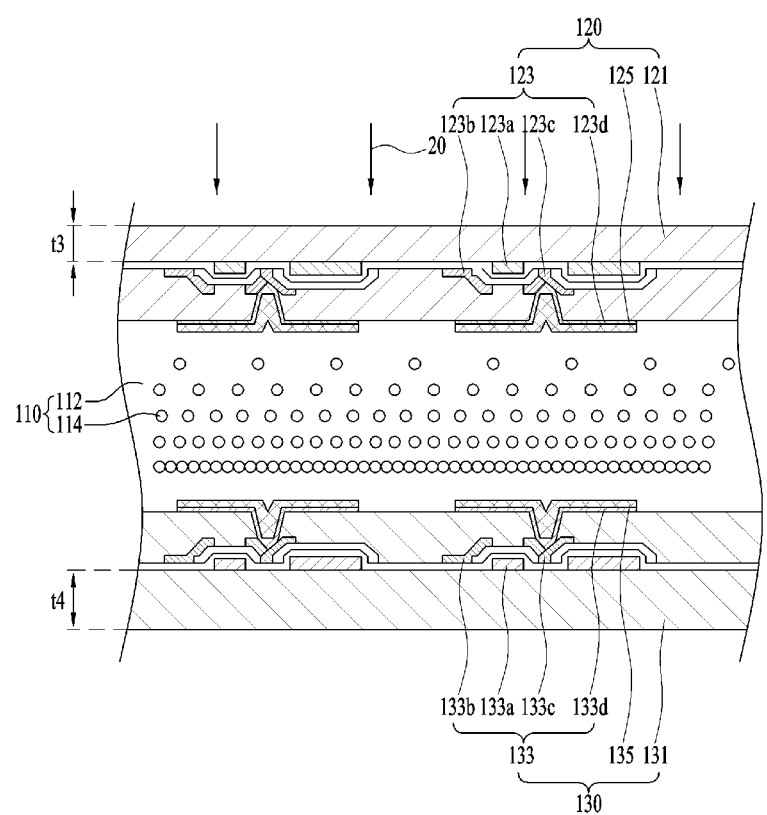

FIGS. 17 to 19 are structural cross-sectional diagrams illustrating an X-ray detector according to the tenth embodiment of the present invention.

As shown in FIGS. 17 to 19, the X-ray detector may include a scintillator layer 110 and a photoelectric conversion module that includes first and second photoelectric converters 120 and 130.

The scintillator layer 110 may convert incident X-rays to light, and may be made of CsI, NaI, LiF, GOS (Gadolinium Oxysulfide), or the like.

The scintillator layer 110 may include a binder resin 112 and a plurality of fluorescent particles 114. In this case, as shown in FIG. 17, the fluorescent particles 114 may be disposed uniformly within the scintillator layer 110.

As the case may be, as shown in FIG. 18, a ratio of the fluorescent particles 114 may be higher in the area adjacent to the lower surface of the scintillator layer 110 than in the area adjacent to the upper surface of the scintillator layer 110. This is because that it may be difficult for the second photoelectric conversion layer 135 disposed on the lower surface of the scintillator layer 110 to detect light 30 as the X-ray incident amount is smaller in the lower area of the scintillator layer 110 than in the upper area of the scintillator layer 110.

As another case, as shown in FIG. 19, the ratio of the fluorescent particles 114 may be increased gradiently from the upper surface of the scintillator layer 110 to the lower surface of the scintillator layer 110. This is because that it may be difficult for the second photoelectric conversion layer 135 disposed on the lower surface of the scintillator layer 110 to detect light 30 as the X-ray incident amount is smaller in the lower area of the scintillator layer 110 than in the upper area of the scintillator layer 110.

As described above, according to the present invention, the ratio of the fluorescent particles 114 may be increased from the upper surface of the scintillator layer 110 to the lower surface of the scintillator layer 110, whereby light detection efficiency may be increased.

FIGS. 20 to 23 are structural cross-sectional diagrams illustrating an X-ray detector according to the eleventh embodiment of the present invention.

As shown in FIGS. 20 to 23, the X-ray detector may include a scintillator layer 110 and a photoelectric conversion module that includes first and second photoelectric converters 120 and 130.

The scintillator layer 110 may have a columnar crystal structure that a plurality of strip shaped columnar crystals are formed from the upper surface to the lower surface. In this case, the columnar crystals may be used as light paths 115 of the scintillator layer 110. For example, the scintillator layer 110 may be provided with a plurality of light paths 115 formed from the upper surface to the lower surface at predetermined intervals. In this way, the light paths 115 are formed in the scintillator layer 110 to detect light 30 condensed on the photoelectric conversion layer only without light loss.

Figure 20:
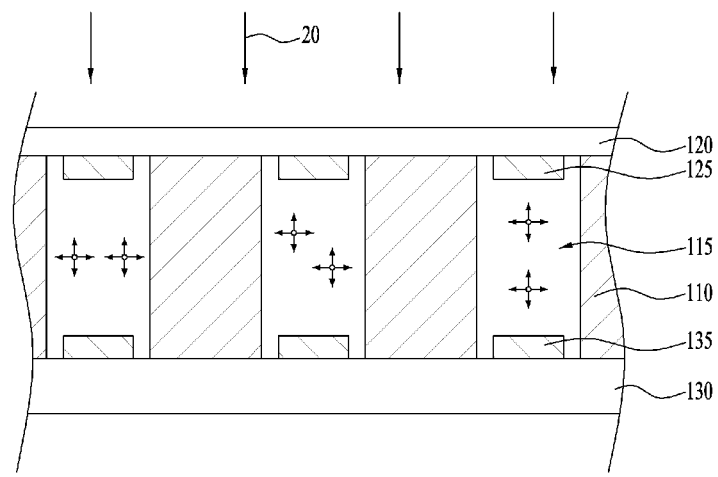
FIGS. 20 to 23 are structural cross-sectional diagrams illustrating an X-ray detector according to the eleventh embodiment of the present invention.

The light paths 115 may be disposed in various arrangements in accordance with an arrangement relation between the first photoelectric conversion layer 125 of the first photoelectric converter 120 and the second photoelectric conversion layer 135 of the second photoelectric converter 130. For example, as shown in FIG. 20, if the first photoelectric conversion layer 125 of the first photoelectric converter 120 and the second photoelectric conversion layer 135 of the second photoelectric converter 130 are disposed to correspond to each other one to one, one side of the light paths 115 may be formed to correspond to the first photoelectric conversion layer 125 of the first photoelectric converter 120 and the other side of the light paths 115 may be formed to correspond to the second photoelectric conversion layer 135 of the second photoelectric converter 130. That is, a front end of the light paths 115 may be opened to correspond to the first photoelectric conversion layer 125 of the first photoelectric converter 120, and a rear end of the light paths 115 may be opened to correspond to the second photoelectric conversion layer 135 of the second photoelectric converter 130.

Figure 21:
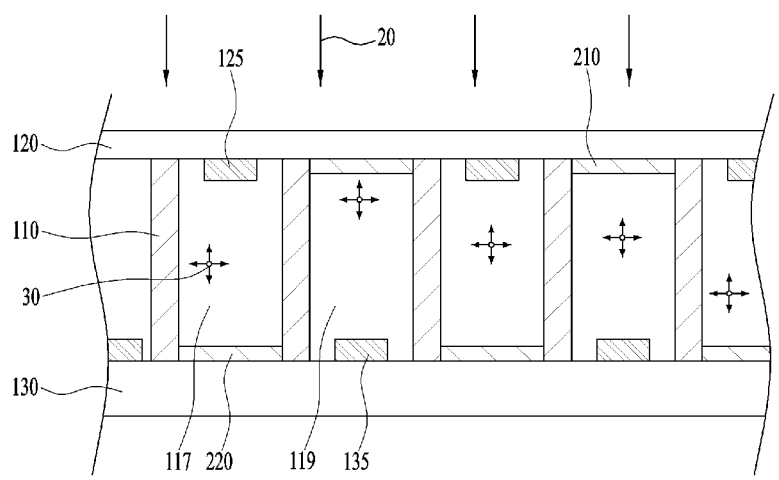

As another case, as shown in FIG. 21, if the first photoelectric conversion layer 125 of the first photoelectric converter 120 and the second photoelectric conversion layer 135 of the second photoelectric converter 130 are disposed alternately with each other, the light paths may include a first light path 117 corresponding to the first photoelectric conversion layer 125 of the first photoelectric converter 120 and a second light path 119 corresponding to the second photoelectric conversion layer 135 of the second photoelectric converter 130. That is, a front end of the first light path 117 may be opened to correspond to the first photoelectric conversion layer 125 of the first photoelectric converter 120, and a rear end of the first light path 117 may be blocked by a first reflective film 220. And, a front end of the second light path 119 may be blocked by a second reflective film 210, and a rear end of the second light path 119 may be opened to correspond to the second photoelectric conversion layer 135 of the second photoelectric converter 130. The first and second reflective films 220 and 210 are formed to increase light detection efficiency by minimizing light loss.

As another case, the first reflective film 220 disposed at the rear end of the first light path 117 and the second reflective film 210 disposed at the front end of the second light path 119 may be removed.

Figure 22:
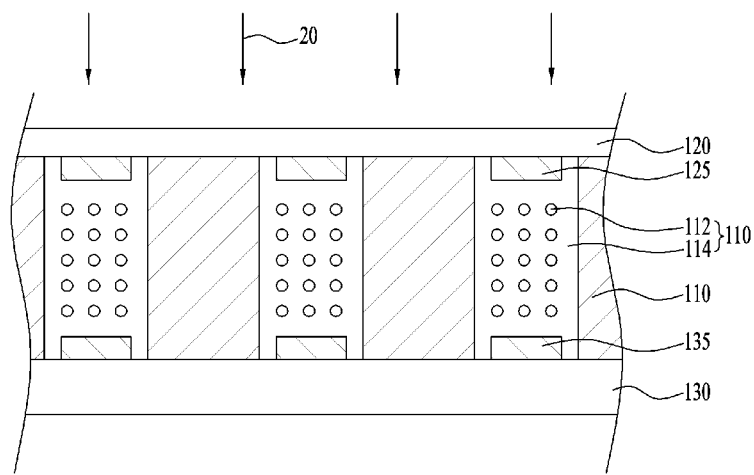

As still another case, as shown in FIG. 22, a plurality of fluorescent particles 114 may be formed inside the light paths 115. The scintillator layer 110 inside the light paths 115 may include a binder resin 112 and a plurality of fluorescent particles 114. In this case, the fluorescent particles 114 may be disposed uniformly within the light paths of the scintillator layer 110.

As the case may be, a ratio of the fluorescent particles 114 may be higher in the area adjacent to the lower surface of the scintillator layer 110 than in the area adjacent to the upper surface of the scintillator layer 110. This is because that it may be difficult for the second photoelectric conversion layer 135 disposed on the lower surface of the scintillator layer 110 to detect light 30 as the X-ray incident amount is smaller in the lower area of the scintillator layer 110 than in the upper area of the scintillator layer 110.

As another case, the ratio of the fluorescent particles 114 may be increased gradiently from the upper surface of the scintillator layer 110 to the lower surface of the scintillator layer 110. This is because that it may be difficult for the second photoelectric conversion layer 135 disposed on the lower surface of the scintillator layer 110 to detect light 30 as the X-ray incident amount is smaller in the lower area of the scintillator layer 110 than in the upper area of the scintillator layer 110.

Figure 23:
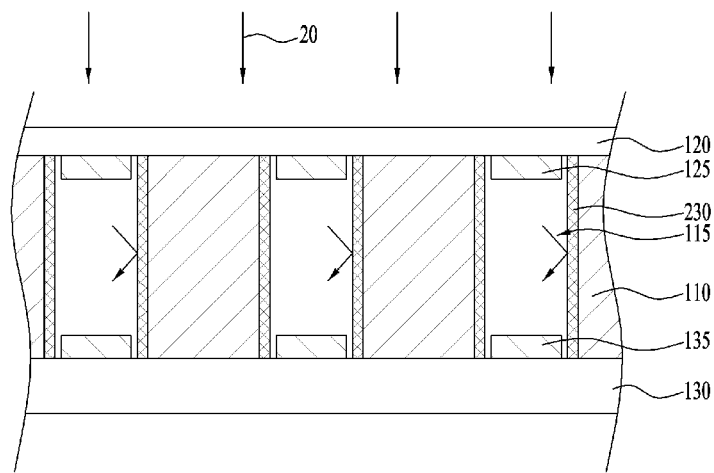

As still another case, as shown in FIG. 23, total reflective films 230 may be formed at inner sides of the light paths 115. In this case, the total reflective films 230 are formed to increase light detection efficiency by minimizing light loss.

As described above, according to the present invention, the total reflective films are disposed at inner sides of the light paths of the scintillator layer to minimize light loss, whereby light detection efficiency may be increased.

Figure 24:
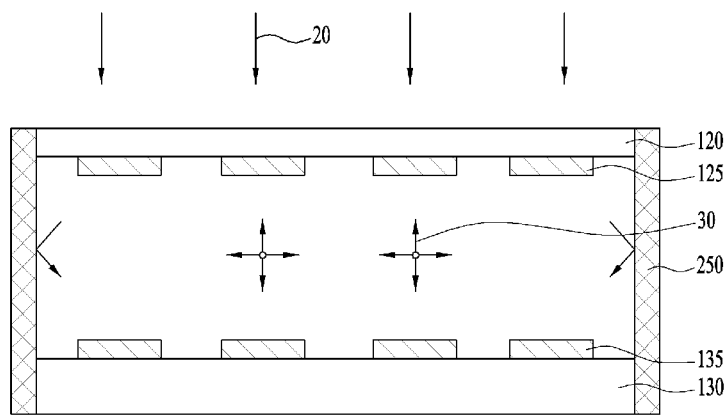
FIGS. 24 and 25 are structural cross-sectional diagrams illustrating an X-ray detector according to the twelfth embodiment of the present invention.
Figure 25:
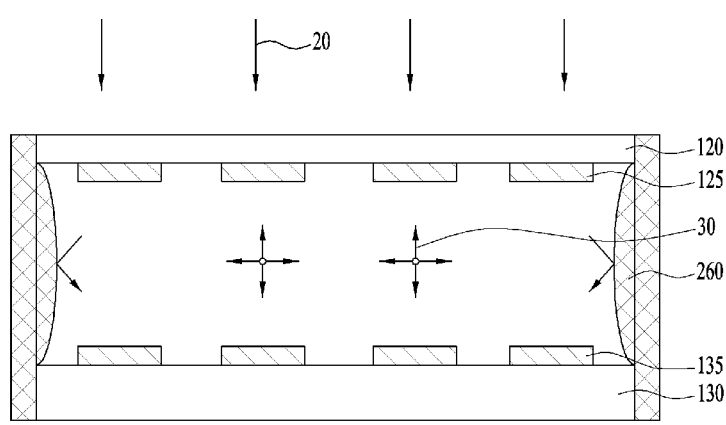

FIGS. 24 and 25 are structural cross-sectional diagrams illustrating an X-ray detector according to the twelfth embodiment of the present invention.

As shown in FIGS. 24 and 25, the X-ray detector may include a scintillator layer 110 and a photoelectric conversion module that includes first and second photoelectric converters 120 and 130.

As shown in FIG. 24, the scintillator layer 110 may be provided with total reflective films 250 disposed at both sides. The total reflective films 250 may have flat shaped surfaces. The total reflective films 250 are formed to block light loss at both sides of the scintillator layer 110 and inwardly reflect light to minimize light loss and increase light detection efficiency.

Also, as shown in FIG. 25, the scintillator layer 110 may be provided with total reflective films 250 disposed at both sides. The total reflective films 250 may have concave surfaces toward inner sides of the scintillator layer 110. This is because that light may be reflected uniformly toward the inner sides of the scintillator layer 110 to increase light detection efficiency.

As described above, according to the present invention, the total reflective films are disposed at both sides of the scintillator layer to minimize light loss, whereby X-ray detection efficiency may be increased.

As described above, according to the present invention, the following advantages may be obtained.

According to the present invention, since the photoelectric converters are respectively disposed on the upper surface and the lower surface of the scintillator layer, detection efficiency of X-rays may be increased, whereby picture quality of an image may be improved.

Also, according to the present invention, the thickness of the photoelectric converter disposed on the upper surface of the scintillator layer may be reduced to enable a slim size and miniaturization.

Also, according to the present invention, the block layer is disposed between the photoelectric conversion layers adjacent to each other to improve picture quality of an image by using a small amount of X-rays, whereby an exposure rate may be minimized.

Also, according to the present invention, the light paths are disposed in the scintillator layer or the total reflective films are disposed at both sides of the scintillator layer to minimize light loss, whereby X-ray detection efficiency may be increased.

Also, according to the present invention, images acquired from the plurality of photoelectric converters are compared with each other to select an image of high quality, or images acquired from the plurality of photoelectric converters are overlapped with each other to acquire an image of high quality regardless of a defect of the photoelectric converters.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An X-ray detector comprising:
a scintillator layer configured for converting externally incident X-rays into light; and
a photoelectric converter configured for converting the converted light into an electric signal,
wherein the photoelectric converter includes:
a first photoelectric converter disposed on an upper surface of the scintillator layer where the X-rays enter; and
a second photoelectric converter disposed on a lower surface of the scintillator layer,
wherein the first photoelectric converter includes:
a first substrate having a plurality of pixel areas;
a first photoelectric conversion layer disposed on the pixel areas of the first substrate, converting light into an electric signal; and
a first transistor disposed between the first substrate and the first photoelectric conversion layer, outputting the converted electric signal,
wherein the second photoelectric converter includes:
a second substrate having a plurality of pixel areas;
a second photoelectric conversion layer disposed on the pixel areas of the second substrate, converting light into an electric signal; and
a second transistor disposed between the second substrate and the second photoelectric conversion layer, outputting the converted electric signal,
wherein the first photoelectric conversion layer and the second photoelectric conversion layer are disposed alternately with each other, and
wherein a first reflective layer is formed between adjacent first photoelectric conversion layers and a second reflective layer is formed between adjacent second photoelectric conversion layers.

2. The X-ray detector according to claim 1, wherein the first photoelectric converter has a thickness different from that of the second photoelectric converter.

3. The X-ray detector according to claim 1, wherein the first substrate of the first photoelectric converter has a thickness thinner than that of the second substrate of the second photoelectric converter.

4. The X-ray detector according to claim 1, wherein X-ray transmittance of the first substrate of the first photoelectric converter is higher than that of the second substrate of the second photoelectric converter.

5. The X-ray detector according to claim 1, wherein the first substrate of the first photoelectric converter includes a block layer disposed between first photoelectric conversion layers adjacent to each other, blocking the incident X-rays.

6. The X-ray detector according to claim 5, wherein the first photoelectric conversion layer is formed on a lower surface of the first substrate, which faces the scintillator layer, and the block layer is formed on an upper surface of the first substrate, where the X-rays enter.

7. The X-ray detector according to claim 1, wherein the first photoelectric conversion layer is formed on a pixel electrode of the first transistor, and the second photoelectric conversion layer is formed on a pixel electrode of the second transistor.

8. The X-ray detector according to claim 1, wherein the first photoelectric conversion layer and the second photoelectric conversion layer are directly in contact with the scintillator layer.

9. The X-ray detector according to claim 1, wherein the first photoelectric conversion layer and the second photoelectric conversion layer are disposed to be spaced apart from the scintillator layer at a certain interval.

10. The X-ray detector according to claim 1, wherein the first photoelectric conversion layer is directly in contact with the scintillator layer, and the second photoelectric conversion layer is disposed to be spaced apart from the scintillator layer at a certain interval.

11. The X-ray detector according to claim 1, wherein the scintillator layer includes a plurality of fluorescent particles.

12. The X-ray detector according to claim 1, wherein the scintillator layer includes a plurality of light paths formed from the upper surface to the lower surface at a predetermined interval,
a front end of each of the light paths is opened to correspond to the first photoelectric conversion layer of the first photoelectric converter, and
a rear end of each of the light paths is opened to correspond to the second photoelectric conversion layer of the second photoelectric converter.

13. An X-ray image system comprising:
an X-ray generator irradiating X-rays to an object to be photographed;
an X-ray detector including:
a scintillator layer;
a first photoelectric converter disposed on an upper surface of the scintillator layer and receiving X-rays passed through the object and converting the X-rays into a first electric signal; and
a second photoelectric converter disposed on a lower surface of the scintillator layer and converting the X-rays into a second electric signal;
a first image processor processing a first image of the object based on the first electric signal of the X-ray detector;
a second image processor processing a second image of the object based on the second electric signal of the X-ray detector;
a display module displaying the first and second processed images of the object; and
a controller controlling the X-ray generator, the X-ray detector, the first and second image processors and the display module,
wherein the scintillator layer located between the first photoelectric converter and the second photoelectric converter is for converting externally incident X-rays into light,
wherein the first photoelectric converter includes:
a first substrate having a plurality of pixel areas;
a first photoelectric conversion layer disposed on the pixel areas of the first substrate, converting light into an electric signal; and a first transistor disposed between the first substrate and the first photoelectric conversion layer, outputting the converted electric signal, wherein the second photoelectric converter includes:
a second substrate having a plurality of pixel areas;
a second photoelectric conversion layer disposed on the pixel areas of the second substrate, converting light into an electric signal; and
a second transistor disposed between the second substrate and the second photoelectric conversion layer, outputting the converted electric signal, wherein the first photoelectric conversion layer and the second photoelectric conversion layer are disposed alternately with each other, and wherein a first reflective layer is formed between adjacent first photoelectric conversion layers and a second reflective layer is formed between adjacent second photoelectric conversion layers.

14. The X-ray image system according to claim 13, wherein the controller synthesizes the first image processed from the first image processor with the second image processed from the second image processor to display a synthesized image on the display module.

15. The X-ray image system according to claim 13, wherein the controller synthesizes some of the first image processed from the first image processor with some of the second image processed from the second image processor to display a synthesized image on the display module.

16. The X-ray image system according to claim 13, wherein the controller compares picture quality of the first image processed from the first image processor with picture quality of the second image processed from the second image processor to display one of the first and second images that has higher picture quality on the display module.

* * * * *